United States Patent [19]
Gustavsson et al.

[11] Patent Number: 5,958,955
[45] Date of Patent: Sep. 28, 1999

[54] METHOD FOR THE SYNTHESIS OF A BENZIMIDAZOLE COMPOUND

[75] Inventors: Anders Gustavsson, Nykvarn; Åke Källström, Södertälje, both of Sweden

[73] Assignee: Astra Aktiebolag, Sodertalje, Sweden

[21] Appl. No.: 08/776,222

[22] PCT Filed: Dec. 5, 1996

[86] PCT No.: PCT/SE96/01603

§ 371 Date: Jan. 23, 1997

§ 102(e) Date: Jan. 23, 1997

[87] PCT Pub. No.: WO97/22603

PCT Pub. Date: Jun. 26, 1997

[30] Foreign Application Priority Data

Dec. 15, 1995 [SE] Sweden .................................. 9504503

[51] Int. Cl.$^6$ ........................ A61K 31/44; C07D 401/12; C07D 403/12

[52] U.S. Cl. ........................ 514/339; 514/338; 546/273.7

[58] Field of Search ..................................... 514/338, 339; 546/273.7

[56] References Cited

U.S. PATENT DOCUMENTS

| 4,255,431 | 3/1981 | Junggren et al. | 514/338 |
| 4,619,997 | 10/1986 | Sih | 544/124 |
| 4,628,098 | 12/1986 | Nohara et al. | 546/271 |
| 4,686,230 | 8/1987 | Rainer et al. | 514/338 |
| 5,391,752 | 2/1995 | Hoerrner et al. | 546/271 |

FOREIGN PATENT DOCUMENTS

| 9118895 | 12/1991 | WIPO . |
| 9722603 | 6/1997 | WIPO . |

*Primary Examiner*—Alan L. Rotman
*Attorney, Agent, or Firm*—White & Case L.L.P.

[57] ABSTRACT

A process for the manufacture of omeprazole from pyrmethyl alcohol via pyrmethyl chloride and pyrmetazole characterized in that the whole reaction sequence is carried out without any isolation or purification of intermediates. Further that the reaction is carried out in a main solvent system common for the whole reaction sequence and inert to the reactants formed during the process and used in the process. The process according to the present invention may also include an additional purification step.

13 Claims, No Drawings

METHOD FOR THE SYNTHESIS OF A BENZIMIDAZOLE COMPOUND

FIELD OF THE INVENTION

The present invention relates to a novel process for the synthesis of 5-methoxy-2-[[(4-methoxy-3,5-dimethyl-2-pyridinyl)-methyl]sulphinyl]-1H-benzimidazole, known under the generic name omeprazole. Moreover, the present invention also relates to manufacture of a pharmaceutical preparation thereof and its use in medicine.

BACKGROUND OF THE INVENTION AND PRIOR ART

Omeprazole is an inhibitor of gastric acid secretion making it useful as an antiulcer agent U.S. Pat. No. 4,255,431 (corresponding to EP 0 005 129) discloses a process for the preparation of this class of substituted benzimidazoles. Said process comprises a couple of reaction steps. The three last steps of the process utilize more than one solvent and requires isolation of intermediates to give the final product omeprazole. The resulting product is contaminated with starting materials and by-products.

WO 91/18895 describes an improved process for synthesis of omeprazole. This process describes the oxidation step and a work-up procedure of omeprazole. The oxidation step utilizes m-chloroperoxybenzoic acid in a methylene chloride/water system at substantially constant pH of about 8.0 to 8.6. The work-up procedure includes crystallization of omeprazole by the addition of an alkyl formate.

Another process for the manufacture of omeprazole is described in U.S. Pat. No. 5,391,752. This process also describes only the oxidation step. Said oxidation step utilizes magnesium monoperoxyphtalate as an oxidazing agent. The resulting product is contaminated with starting material and by-products.

Yet another process for the manufacture of compounds showing structural similarities to omeprazole is disclosed in U.S. Pat. No. 4,619,997. The intermediates are isolated, but not purified, and different solvent systems are used in the chemical steps throughout the process.

In the light of the above there was still a need for a new convenient and more efficient process to manufacture omeprazole.

SUMMARY OF THE INVENTION

In the following the improved process is described. Scheme I below describes three main reaction sequences in the manufacture of omeprazole. In the scheme the complete chemical names as well as short names for the starting material and the different intermediates are stated. The starting material as well as the reactants used are readily available by procedures described in the literature.

Scheme I

Step 1:

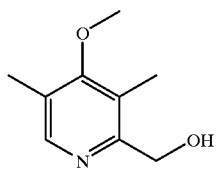

(4-Methoxy-3,5-dimethyl-2-pyridinyl)methyl alcohol (Pyrmethyl alcohol)  +  SOCl₂ (or another suitable chlorinating agent)

→

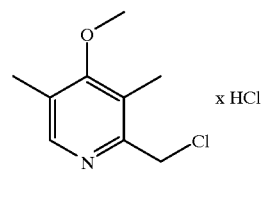

(4-Methoxy-3,5-dimethyl-2-pyridinyl)methyl chloride (Pyrmethyl chloride)

Step 2:

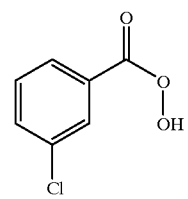

(4-Methoxy-3,5-dimethyl-2-pyridinyl)methyl chloride (Pyrmethyl chloride)  +

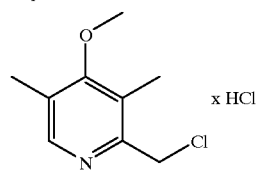

2-Mercapto-5-methoxybenzimidazole (Metmercazole)

$\xrightarrow{\text{base}}$

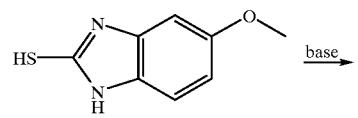

5-Methoxy-2(((4-methoxy-3,5-dimethyl-2-pyridinyl)-methyl)-thio)-1H-benzimidazole (Pyrmetazole)

Step 3:

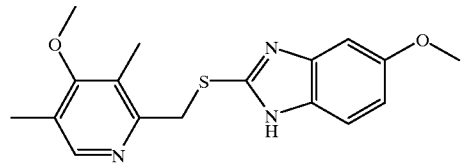

5-Methoxy-2(((4-methoxy-3,5-dimethyl-2-pyridinyl)-methyl)-thio)-1H-benzimidazole (Pyrmetazole)

+

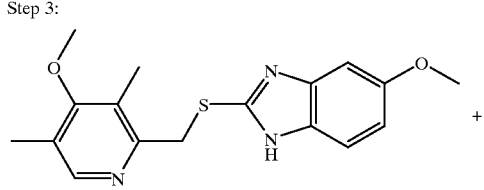

m-Chloroperoxybenzoic acid

→

-continued

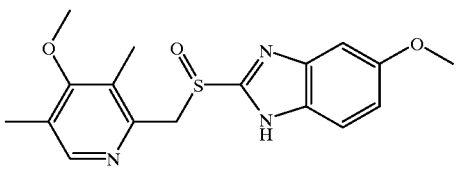

5-Methoxy-2(((4-methoxy-3,5-dimethyl-2-pyridinyl)-methyl)-sulfinyl)-1H-benzimidazole (Omeprazole)

Scheme I

Advantages of the improved process of the present invention are disclosed in the following paragraphs.

One object of the present invention is to provide a process for the manufacture of omeprazole with all three reaction steps, described above, being carried out without any isolation or purification of the intermediates, and carried out in one main solvent system common for the whole sequence. Such a process eliminates time consuming steps for isolation or purification of intermediates or solvent change in the process and thus making the process more efficient with a high production capacity. A further important benefit of such a process is that the handling of toxicological and suspected mutagenic intermediates such as pyrmethyl chloride, due to isolation or purification, is eliminated.

Another preferred object of the present invention is to provide a process utilizing a solvent system which is environmentally friendly to avoid outlet of harmful solvents. There is a general interest from environmental groups both inside and outside the pharmaceutical industry that the industry shall develop and use environmentally friendly processes. In some countries the authorities also have made restrictions on the outlet of harmful chlorinated solvents into the air.

Surprisingly, the novel process of the present invention gives omeprazole in a high purity without any isolation or purification of intermediates. The omeprazole obtained may optionally be further processed in a purification step and/or optionally processed into pharmaceutically acceptable salts.

Another object of the present invention is to provide a process for an optional purification step of omeprazole.

Further, the present reaction sequence starting from pyrmethyl alcohol via pyrmethyl chloride and pyrmetazole giving omeprazole can be carried out in a main solvent system used through the whole reaction sequence. The solvent system is preferably inert against all reactants and suitable for the three process steps.

DETAILED DESCRIPTION OF THE INVENTION

In step 1 pyrmethyl alcohol is reacted with an excess of thionyl chloride or another suitable chlorinating agent giving alkyl chlorides, i.e. pyrmethyl chloride. The reaction is preferably carried out at ambient temperature and for approximately a period of 30 minutes. The reaction may also be performed at a temperature of −5° C. to 25° C.

The reaction is carried out in a solvent system, which is used throughout the whole reaction sequence described in scheme I, i.e. from pyrmethyl alcohol to omeprazole. Such a solvent system suitable for the present process comprises a main solvent and optionally one or more co-solvents. The main solvent is preferably water immiscible, e.g. carbontetrachloride, 1,1,2-trichloroethane, chloroform, methylene chloride or toluene. Toluene is especially preferred from an environmental point of view.

Furthermore, the solvent system may optionally comprise co-solvent(s) to further improve/enhance the solubility of the reactants or products during the whole reaction sequence. The solvent system will function without any addition of a co-solvent, but the addition of such a co-solvent will enhance the process capacity, i.e. the yield per volume. Preferred co-solvents are alcohols and especially a lower alcohol comprising 1–4 carbon atoms, which carbon chain may be branched or straight.

Examples of solvent systems include, but are not limited to, 70–80% (by volume) methylene chloride or toluene and 20–30% (by volume) lower alcohol, e.g. ethanol.

In step 2, the pyrmethyl chloride formed in step 1 is reacted with metmercazole under alkaline conditions, e.g. an alkaline aqueous solution of metmercazole is prepared and mixed with the pyrmethyl chloride in the presence of a phase transfer catalyst. The reaction is preferably carried out at a temperature of 30–60° C. during a prolonged period of time.

Metmercazole is charged in approximately stoichiometric amount to the pyrmethyl chloride. A phase transfer catalyst may be used, for instance a tertiary amine, preferably tetrabutylammonium bromide.

The two phases formed are separated and the aqueous phase may be extracted with the used water immiscible organic solvent, such as methylene chloride or toluene. Furthermore, an alcohol may be added to the pyrmetazole solution to improve the solubility of the formed intermediate, pyrmetazole.

In step 3, m-chloroperoxybenzoic acid is dissolved in an water immiscible organic solvent such as methylene chloride or toluene. The m-chloroperoxybenzoic acid is charged to the obtained pyrmetazole in a buffered two phase system, consisting of the water immiscible solvent, such as methylene chloride or toluene, and aqueous base, such as sodium or potassium hydrogencarbonate. The organic solvent may optionally be diluted with an alcohol to enhance the solubility of the m-chloroperoxybenzoic acid. The oxidation with m-chloroperoxybenzoic acid is preferably performed between 0° and 25° C. The obtained product is extracted into an alkaline, aqueous phase and the formed product is precipitated from the aqueous phase by lowering the pH of the solution to approximately 9 at ambient temperature. Omeprazole is isolated and washed. The overall yield in the process is usually higher than 75%.

The additional purification can be carried out by crystallization from one or several organic solvents, or by precipitation from alkaline water by lowering the pH through addition of an acid or an alkyl formate.

Examples of suitable acids include, but are not limited to, carboxylic acids such as formic acid, acetic acid, or citric acid, and mineral acids, such as hydrogen chloride, hydrogen bromide, hydrogen fluoride, hydrogen iodide, sulfuric acid, nitric acid, or phosphoric acid. Preferred acids are carboxylic acids. Suitable alkyl formats include, but are not limited to, methyl formate and ethyl formate. A preferred alkyl formate is methyl formate.

The present invention is described more in detail in the following non-limiting examples.

Manufacturing of omeprazole

EXAMPLE 1

17.8 g (0.15 mol) Thionyl chloride in 13 mL methylene chloride was charged to a methylene chloride solution of 16.8 g (0.10 mol) pyrmethyl alcohol at ambient temperature. The solution was stirred for approximately 30 minutes.

18.0 g (0.10 mol) Metmercazole, 47.3 g (0.58 mol) aqueous sodium hydroxide (50% w/w) and tetrabutylammonium bromide (0.9 g) were mixed at ambient temperature. The pyrmethyl chloride solution was added at a temperature between 25°–40° C. and the mixture was refluxed for 1–2 hours. The two phases were separated and the aqueous phase was washed with methylene chloride. The organic phases were combined.

10.4 g (0.10 mol) Potassium bicarbonate dissolved in water was added to the pyrmetazole solution.

22.3 g (0.099 mol) Meta-chloroperoxybenzoic acid (76.5% w/w) dissolved in 42 mL of methylene chloride and 10 mL of ethanol were charged to the prepared mixture of pyrmetazole in methylene chloride and potassium bicarbonate in water. The oxidation was carried out at 0–15° C. The product was extracted into the aqueous phase at an alkaline pH by addition of sodium hydroxide. The two phases were separated and the organic phase was washed with an alkaline water solution. The aqueous phases were combined.

Omeprazole was precipitated from the aqueous phase by the addition of 12 mL methyl formate, filtered and washed with water/methanol and dried. Omeprazole was obtained in a yield of 76%.

EXAMPLE 2

13.1 g (0.11 mol) Thionyl chloride was charged to a toluene solution of 16.7 g (0.10 mol) pyrmethyl alcohol at ambient temperature. The reaction was continued for approximately 30 minutes.

The formed pyrmethyl chloride in toluene was mixed with an alkaline aqueous solution of 18.0 g (0.10 mol) metmercazole. The reaction was performed in the presence of 0.9 g tetrabutylammonium bromide at 40° C. during a couple of hours. The two phases were separated and the aqueous phase was extracted with toluene. Ethanol was added to improve the solubility of the resulting product before the solution was cooled to ambient temperature.

24.4 g (0.10 mol) Meta-chloroperoxybenzoic acid in 42 mL toluene and 10 mL ethanol were charged to a two phase system prepared from the obtained pyrmetazole toluene solution, and potassium bicarbonate (13.8 g) in water (120 mL). The oxidation was performed between 0° C. and room temperature. The product was extracted into an alkaline aqueous phase by the addition of sodium hydroxide. The two phases were separated and the organic phase was washed with water. Omeprazole was precipitated by lowering the pH of the solution to approximately 9 at ambient temperature. Omeprazole was isolated, washed, and dried. The overall yield was approximately 77%.

Additional purification of omeprazole

EXAMPLE 3

20.0 g (0.0579 moles) of omeprazole, prepared according to Example 1, 125 mL of methanol and 54 mL of water were mixed at ambient temperature.

The product was dissolved at an alkaline pH by addition of sodium hydroxide. The solution was filtered and cooled to approximately 0° C.

The product was precipitated by addition of diluted acetic acid, filtered and washed with water/methanol, and thereafter dried. Omeprazole was obtained in a yield of 90%.

EXAMPLE 4

11.2 g (0.0324 moles) of omeprazole, prepared according to Example 1, 69 mL of s methanol, 34 mL of methylene chloride and 0.3 mL of ammonia were mixed at ambient temperature and the obtained solution was filtered.

The product was precipitated by evaporation of methylene chloride under reduced pressure.

0.3 mL of ammonia was added and the slurry was cooled to 0° C.

The product was filtered, washed with methanol containing approximately 1% v/v of ammonia, and dried. Omeprazole was obtained in a yield of 90%.

With respect to the environmental point of view, the best way to carry out one aspect of the present invention is according to the process described in Example 2.

We claim:

1. A process for the manufacture of 5-methoxy-2-[[(4-methoxy-3,5-dimethyl-2-pyridinyl)-methyl]sulphinyl]-1H-benzimidazole from (4-methoxy-3,5-dimethyl-2-pyridinyl)-methyl alcohol comprising the following reaction steps Step 1:

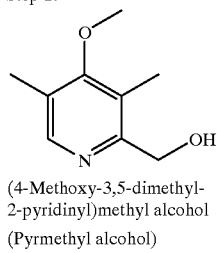

(4-Methoxy-3,5-dimethyl-
2-pyridinyl)methyl alcohol
(Pyrmethyl alcohol)     +

SOCl₂(or another suitable chlorinating agent) ⟶

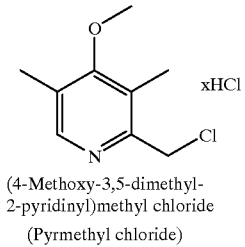

(4-Methoxy-3,5-dimethyl-
2-pyridinyl)methyl chloride
(Pyrmethyl chloride)

Step 2:

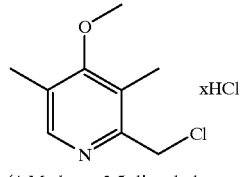

(4-Methoxy-3,5-dimethyl-
2-pyridinyl)methyl chloride   +
(Pyrmethyl chloride)

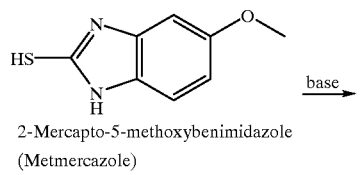

2-Mercapto-5-methoxybenimidazole
(Metmercazole)

-continued

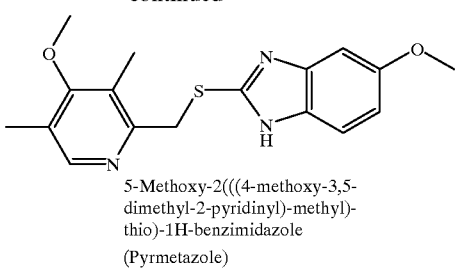

5-Methoxy-2(((4-methoxy-3,5-
dimethyl-2-pyridinyl)-methyl)-
thio)-1H-benzimidazole (Pyrmetazole)

Step 3:

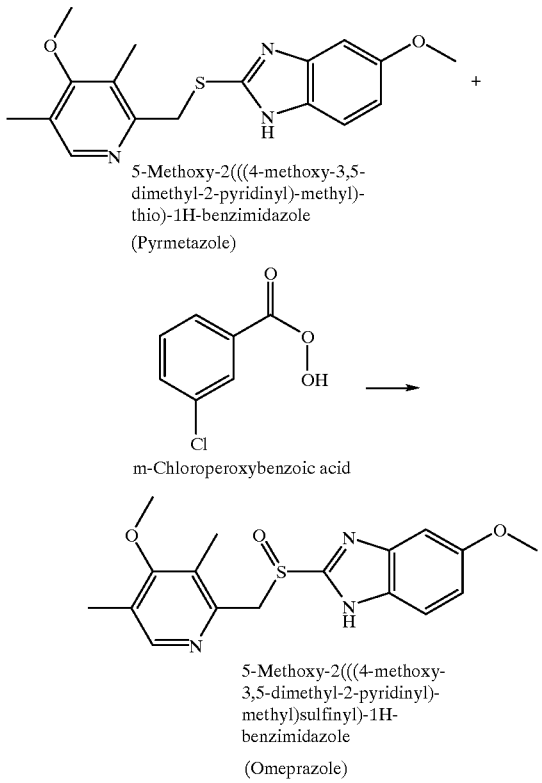

5-Methoxy-2(((4-methoxy-3,5-
dimethyl-2-pyridinyl)-methyl)-
thio)-1H-benzimidazole (Pyrmetazole)

m-Chloroperoxybenzoic acid

5-Methoxy-2(((4-methoxy-
3,5-dimethyl-2-pyridinyl)-
methyl)sulfinyl)-1H-
benzimidazole (Omeprazole)

wherein the reaction steps are carried out in a consecutive order without isolation of the intermediates formed during the process, and wherein one main solvent system common for the whole reaction sequence is used.

2. The process according to claim 1, wherein the solvent system comprises a main solvent and optionally one or more co-solvents.

3. The process according to claim 2, wherein the main solvent is methylene chloride.

4. The process according to claim 2, wherein the main solvent is toluene.

5. The process according to claim 2, wherein the co-solvent is an alcohol.

6. The process according to claim 1, wherein step 1 is carried out at a temperature between −5° C. to 25° C.

7. The process according to claim 1, wherein step 2 is carried out with a phase transfer catalyst.

8. The process according to claim 7, wherein the phase transfer catalyst is tetrabutylammonium bromide.

9. The process according to claim 1, wherein step 2 is carried out at a temperature between 30° C. to 60° C.

10. The process according to any one of the proceeding claims wherein the resulting 5-methoxy-2-[[(4-methoxy-3, 5-dimethyl-2-pyridinyl)-methyl]sulphinyl]-1H-benzimidazole is further purified in a purification step.

11. The process according to claim 10, wherein the purification step involves crystallization from one or several organic solvents.

12. The process according to claim 10, wherein the purification step involves precipitation from alkaline water by lowering the pH through addition of an acid or an alkyl formate.

13. The process according to claim 1, wherein the reaction product of the whole reaction sequence is 5-methoxy-2-[[(4-methoxy-3,5-dimethyl-2-pyridinyl)-methyl]sulphinyl]-1H-benzimidazole.

* * * * *